United States Patent [19]

Arkwright et al.

[11] Patent Number: 5,109,116
[45] Date of Patent: Apr. 28, 1992

[54] IMMUNOSUPPRESSIVE GLYCOPROTEIN

[75] Inventors: Peter D. Arkwright; Raymond A. Dwek; Christopher W. G. Redman, all of Oxford; Graham A. W. Rook, London; Thomas W. Rademacher, Oxford, all of United Kingdom

[73] Assignee: Monsanto Company, St. Louis, Mo.

[21] Appl. No.: 384,233

[22] Filed: Jul. 24, 1989

[51] Int. Cl.⁵ .................. C07K 3/00; C07K 13/00; C07K 15/00; A61K 37/10
[52] U.S. Cl. .................. 530/395; 435/68.1; 514/8; 530/350; 530/412; 530/417
[58] Field of Search ............ 424/85.1, 85.2; 530/350, 351, 395, 412, 413, 417; 435/68.1; 514/8

[56] References Cited

U.S. PATENT DOCUMENTS 4,977,244 12/1990 Muchmore et al. .............. 530/350

OTHER PUBLICATIONS

Streilein and Wegmann, Immunol. Today 8, 362-366 (1987).
Hunziker and Wegmann, CRC Critical Rev. Immunol. 6, 245-285 (1986).
Chaouat and Monnot, Am. J. Reprod. Immunol. 6, 5-8 (1984).
Mowbray et al., Lancet, Apr. 27, 1987, pp. 941-943.
Jenkins et al., Brit. Med. J. 1, 542-544 (1978).
Muchmore & Decker, Science 229, 479-481 (1985).
Muchmore & Decker, J. Immunol. 138, 2541-2546 (1987).
Muchmore et al., J. Immunol. 138, 2547-2553 (1987).
Hession et al., Science, 237, 1479-1484 (1987).
Smith et al, Nature 252, 302-303 (1974).
Pennica et al, Science 236, 83-88 (1987).

Primary Examiner—David L. Lacey
Assistant Examiner—Gian P. Wang
Attorney, Agent, or Firm—Scott J. Meyer; James W. Williams, Jr.

[57] ABSTRACT

The disclosure describes novel immunosuppressive agents isolated from syncytiotrophoblast microvilli membranes by preparing a minutely subdivided and solubilized preparation of said membranes and isolating the unreduced N-linked oligosaccharides from an extract of the preparation.

1 Claim, 13 Drawing Sheets

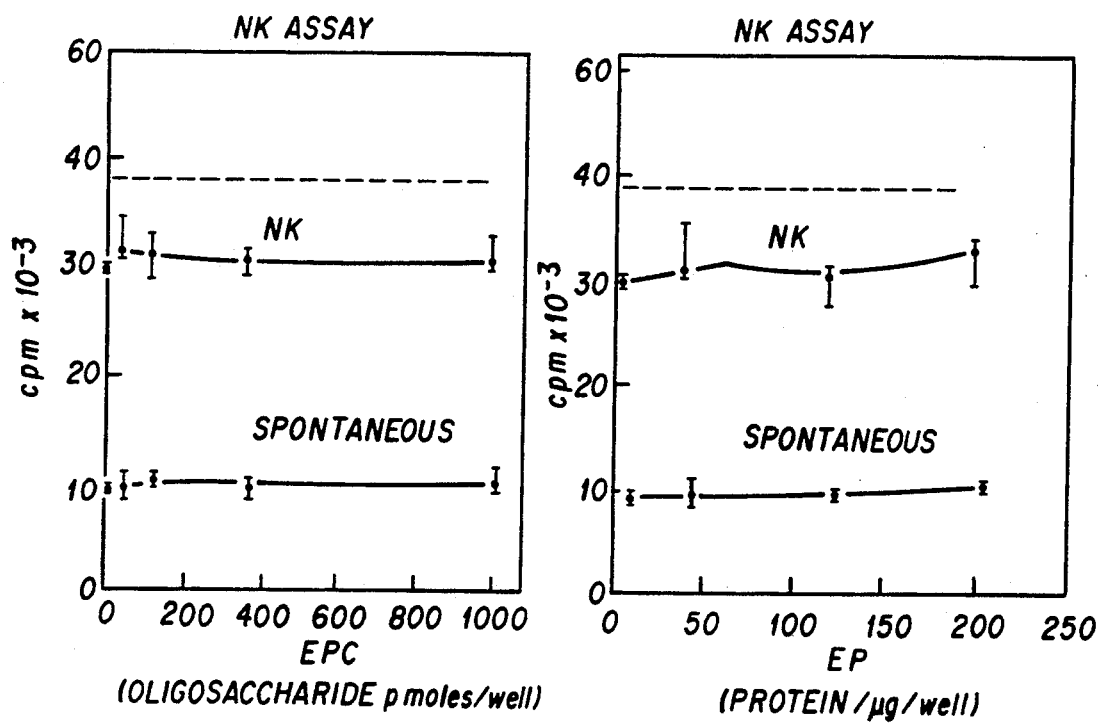
FIG. 8(a)1  FIG. 8(a)2
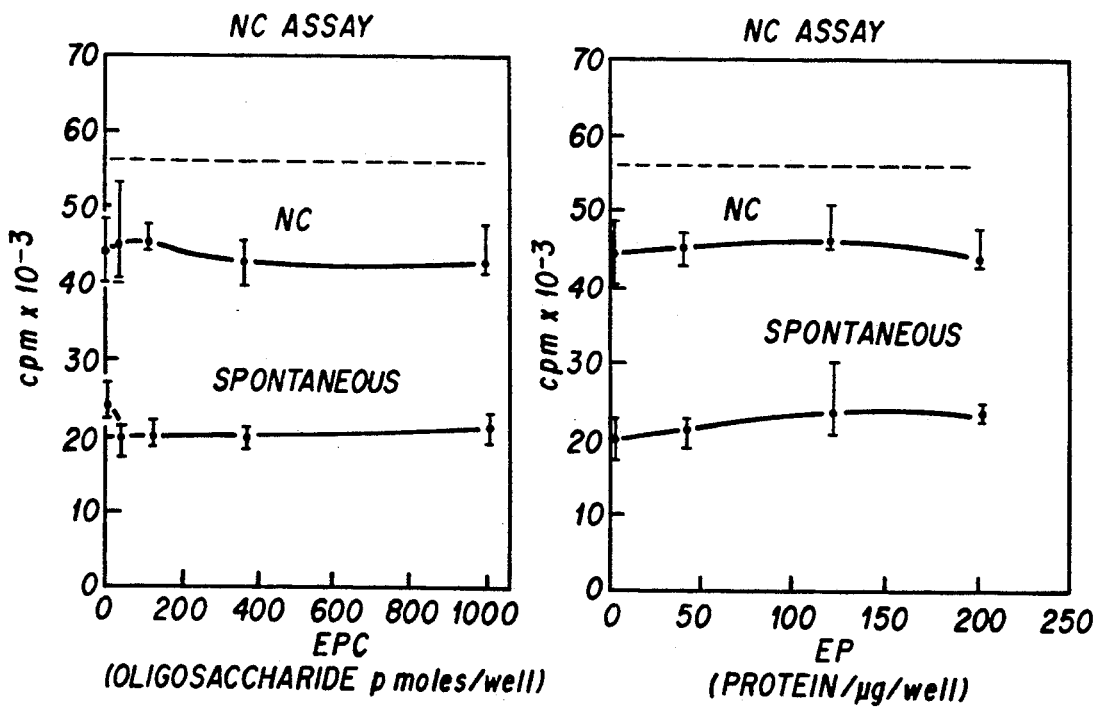
FIG. 8(b)1  FIG. 8(b)2

IMMUNOSUPPRESSIVE GLYCOPROTEIN

BACKGROUND OF THE INVENTION

This invention relates to novel immunosuppressive agents and a method for their production from syncytiotrophoblast microvilli membranes.

The syncytiotrophoblast is the outer syncytial layer of the trophoblast, which is an extraembryonic tissue that supplies nutrition to the embryo. The syncytiotrophoblast cell membrane has a large surface area due to microvillous folding of the membarane which communicates with the maternal blood lakes.

Increasing evidence indicates that local active suppression of the maternal immune response is important for foetal allograft survival. See Streilein and Wegmann, *Immunol. Today* 8, 362-366 (1987); Hunziker and Wegmann, *CRC Critical Rev. Immunol.* 6, 245-285 (1986); Chaoulat and Monnot, *Am. J. Reprod. Immunol.* 6, 5-8 (1984); Mowbray et al., *Lancet, Apr.* 27, 1985, pp. 941-943; Wegmann et al, *Proc. Natl. Acad, Sci, U.S.A.* 76, 2410-2414 (1979); and Jenkins et al., *Brit. Med. J.* 1, 542-544 (1978).

Elucidation of a suppressive mechanism which allows maternal recognition of foetal antigens by the maternal immune response system without deleterious immunopathology would be a desirable goal.

Accordingly, isolation of immunosuppressive substances from placental sources would have significant value for understanding of both successful and unsuccessful (pre-eclampsia) foetal allografts and for the development of various immunosuppressive agents for therapeutic use.

An immunosuppressive glycoprotein termed uromodulin has been isolated heretofor from human pregancy urine. Muchmore and Decker, *Science* 229, 479 (1985). Carbohydrate moieties derived from this glycoprotein were subsequently shown to be immunosuppressive in the absence of intact protein. Muchmore et al., *J. Immunology* 138, 2541-2546 (1987).

BRIEF DESCRIPTION OF THE INVENTION

The present invention concerns novel immunosuppressive agents isolated from syncytiotrophoblast microvilli membranes. According to a method of production in one embodiment of the invention, the microvilli membranes are minutely subdivided and solubilized and the unreduced N-linked oligosaccharides are isolated from an extract of the resulting preparation named EPC.

In other embodiments of the invention, an extrinsic glycoprotein fraction from the syncytiotrophoblast membrane (EP) inhibited mixed lymphocyte reactions (MLRs) and the free oligosaccharides (EPC) derived from this glycoprotein fraction blocked this effect. This effect could also be blocked by the addition of Interleukin-2 (IL-2) to cell cultures. Neither the EP nor the EPC preparation had any effect on Natural Killer cell (NK) and Natural Cytotoxic cell (NC) assays, nor did these preparations effect phorbal ester/A23187 induced T cell activation. In contrast, the EP preparation was found to enhance the cytotoxic effect of tumor necrosis factor (TNF) and this effect was blocked by the free oligosaccharides. This suggests that extrinsic glycoproteins on the syncytiotrophoblast membrane help to mediate focal foetal allograft immunosuppression through the regulation of specific cytokine activities, and that the attached oligosaccharides are important in determining the clinical outcome of this activity. This is consistent with the understanding that the function of oligosaccharides should not be considered in isolation, but in conjunction with the protein to which they are attached. See Rademacher and Dwek, *CIBA Foundation Symposia*, pp. 241-256 (1989); Rademacher et al., *Ann. Rev. Biochem.* 57, 785-838 (1988).

The novel immunosuppressive agents of the present invention thus have various potential therapeutic uses of which the following are illustrative:

I. Use of oligosaccharides (EPC) (monovalent).
   A. Treatment of toxic and cachectic syndromes where cytokines (e.g. TNF) are implicated.
      Examples:
      1) Malignancy
      2) Pre-eclamptic toxaemia
      3) Septic shock
      4) Liver disease
      5) Respiratory Distress Syndrome
   B. Chemotherapy of Immunosuppressed states.
      Examples:
      1) Malignancy-associated immuno-suppression
      2) Iatrogenic immune-suppression (i.e. drugs)

II. Use of glycoprotein (EP) or multivalent (EPC) oligosaccharides.
   A. Treatment of patients with graft vs host reactions (Transplants)
   B. Treatment of patients with host vs graft reactions (Transplants)
   C. Treatment of malignant disease via activation of TNF.

DETAILED DESCRIPTION OF THE INVENTION

While the specification concludes with claims particularly pointing out and specifically claiming the subject matter regarded as forming the present invention, it is believed that the invention will be better understood from the following detailed description of preferred embodiments taken in conjunction with the accompanying drawings in which, briefly:

Figure 5A:
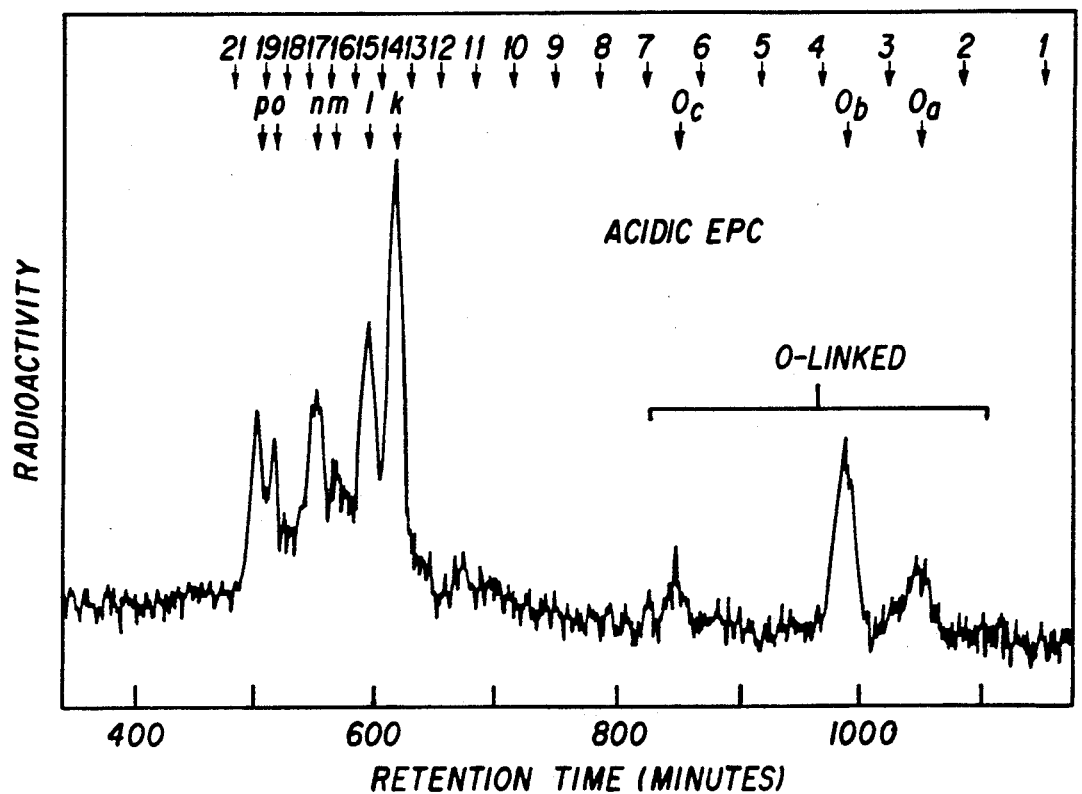
Figure 5B:
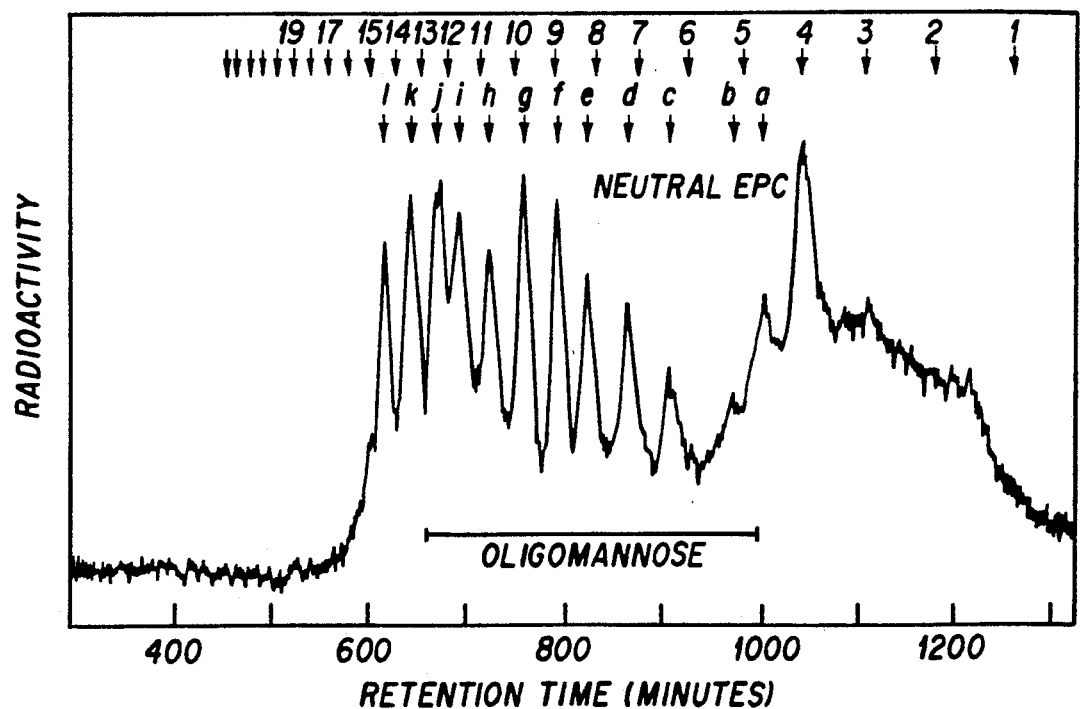
Figure 6A:
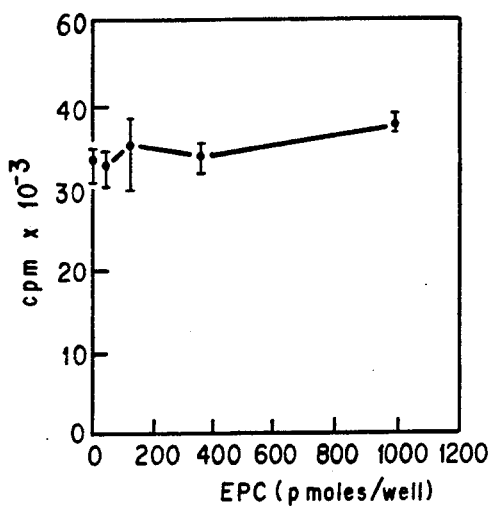
Figure 6B:
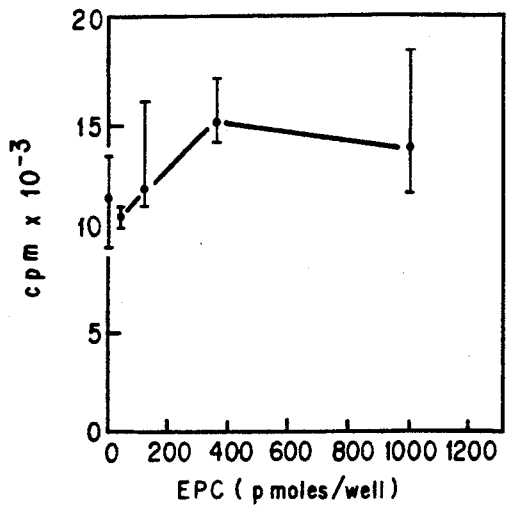
Figure 6C:
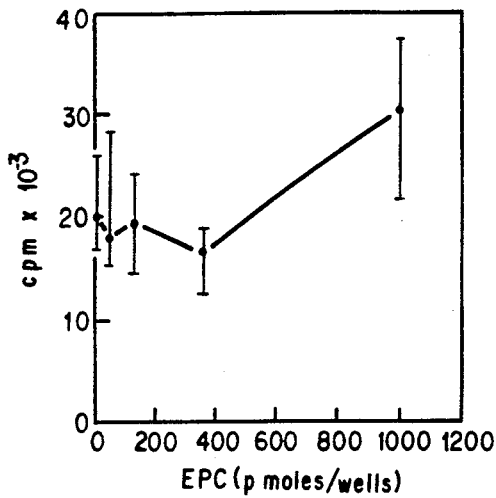
Figure 6D:
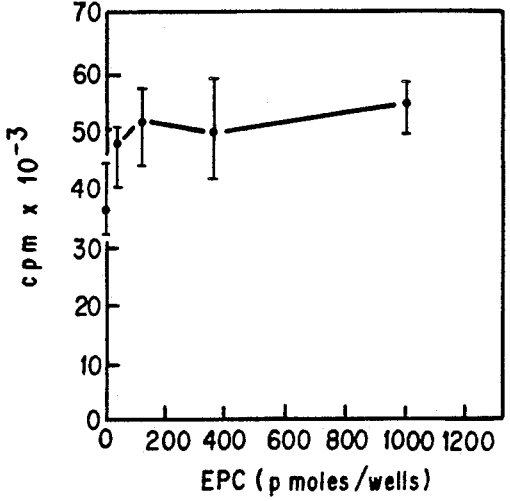
Figure 6E:
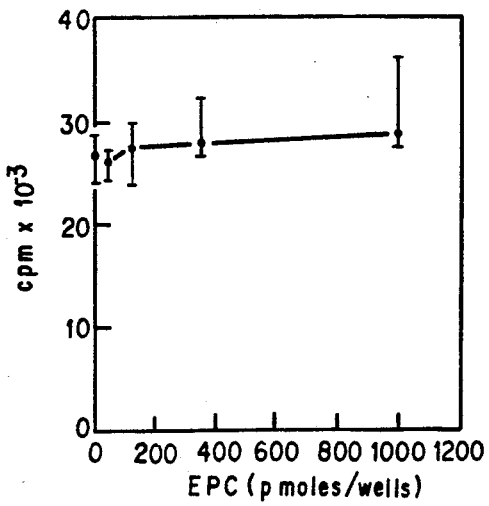
Figure 6F:
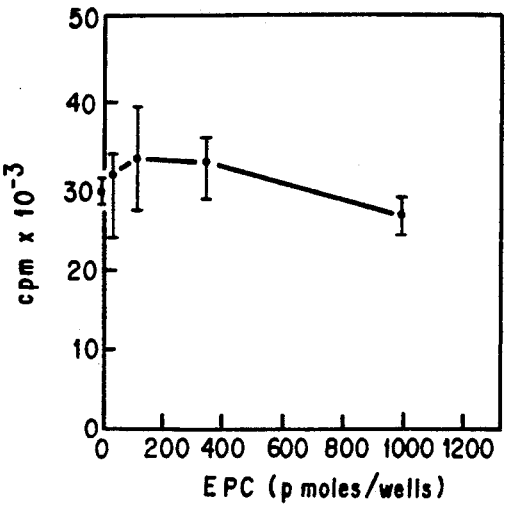

FIG. 5, in two parts FIG. 5(a) and FIG. 5(b), is a graphical representation which shows the unreduced glycan library fractionated into FIG. 5(a) acidic oligosaccharides (Acidio EPC) and FIG. 5(b) neutral oligosaccharides (Neutral EPC).

FIG. 6, in six parts FIG. 6(a), FIG. 6(b), FIG. 6(c), FIG. 6(d), FIG. (f), is a graphical representation whch shows the effect of the syncytiotrophoblast glycan library (EPC) on six different MLRs in FIGS. 6(a) to 6(f), respectively.

Figure 7B:
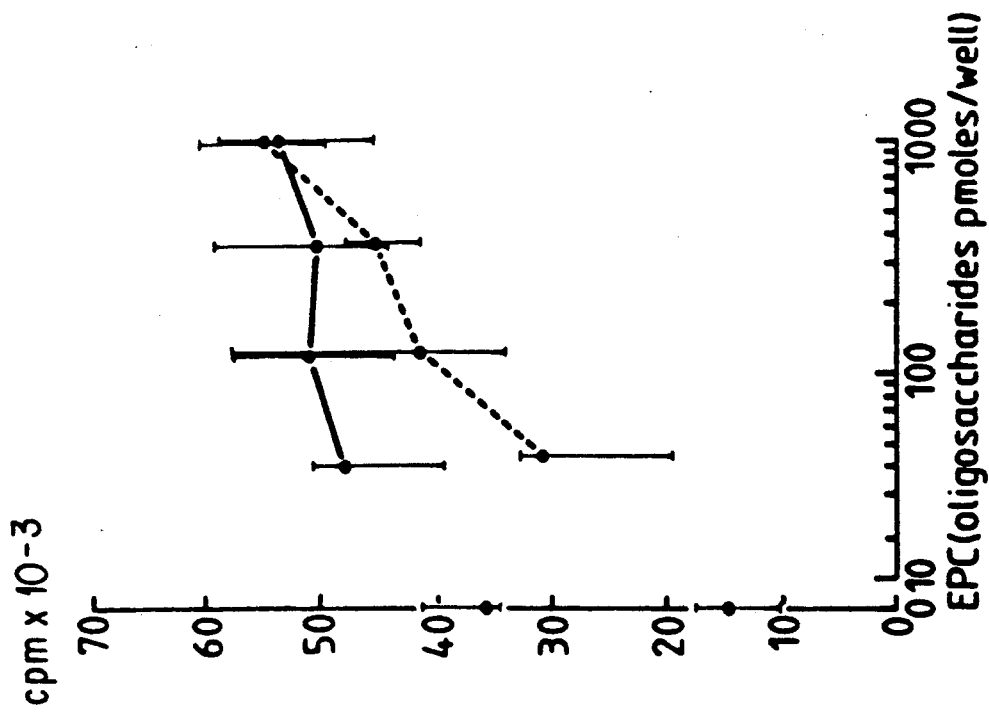
Figure 7A:
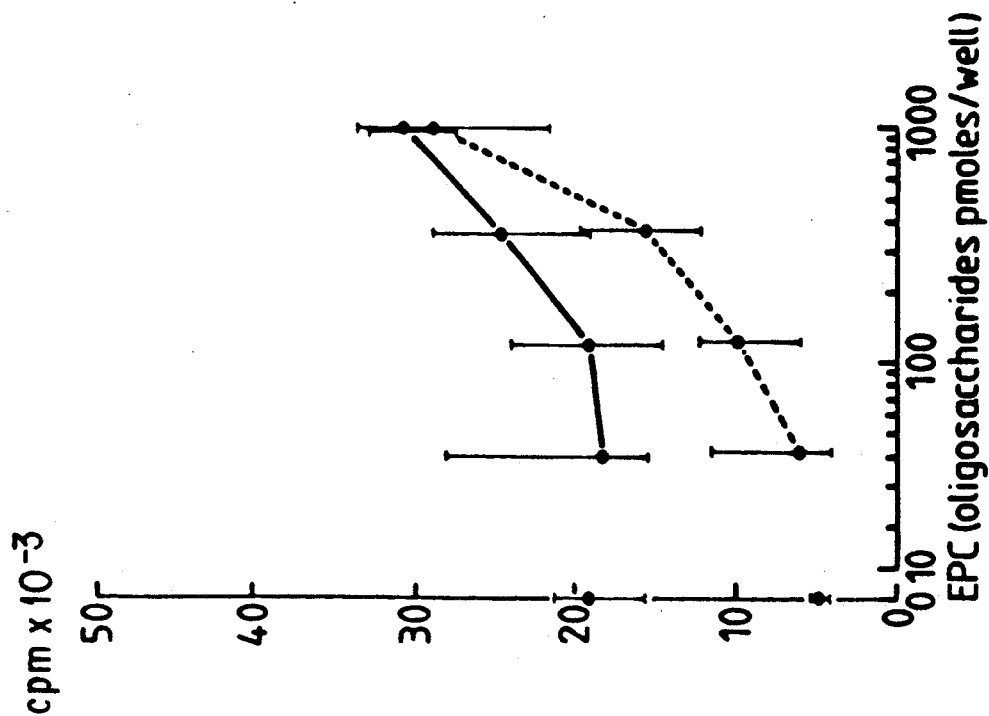

FIG. 7, in two parts FIG. 7(a) and FIG. 7(b), is a graphical representation which shows the effect of syncytiotrophoblast glycan library (EPC) alone (solid line) and in conjunction with 100 μg EP (dotted line) on two different MLRs in FIG. 7(a) and FIG. 7(b), respectively.

Figure 1:
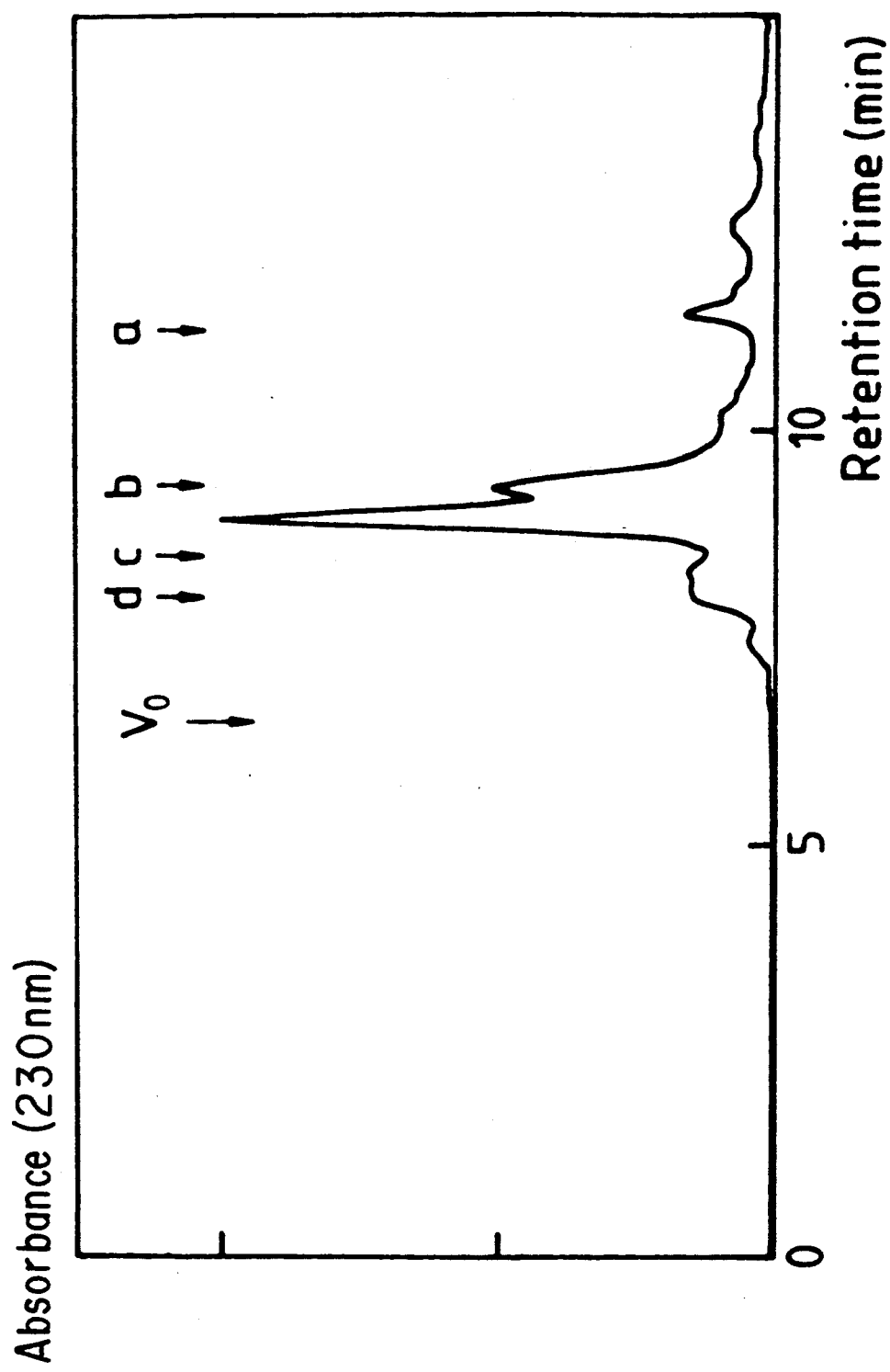
FIG. 1 is a graphical representation which shows the HPLC chromatogram of the extrinsic glycoprotein preparation isolated from syncytiotrophoblast microvilli membranes in one embodiment of the invention, using a Zorbax GF250 HPLC column.
Figure 2:
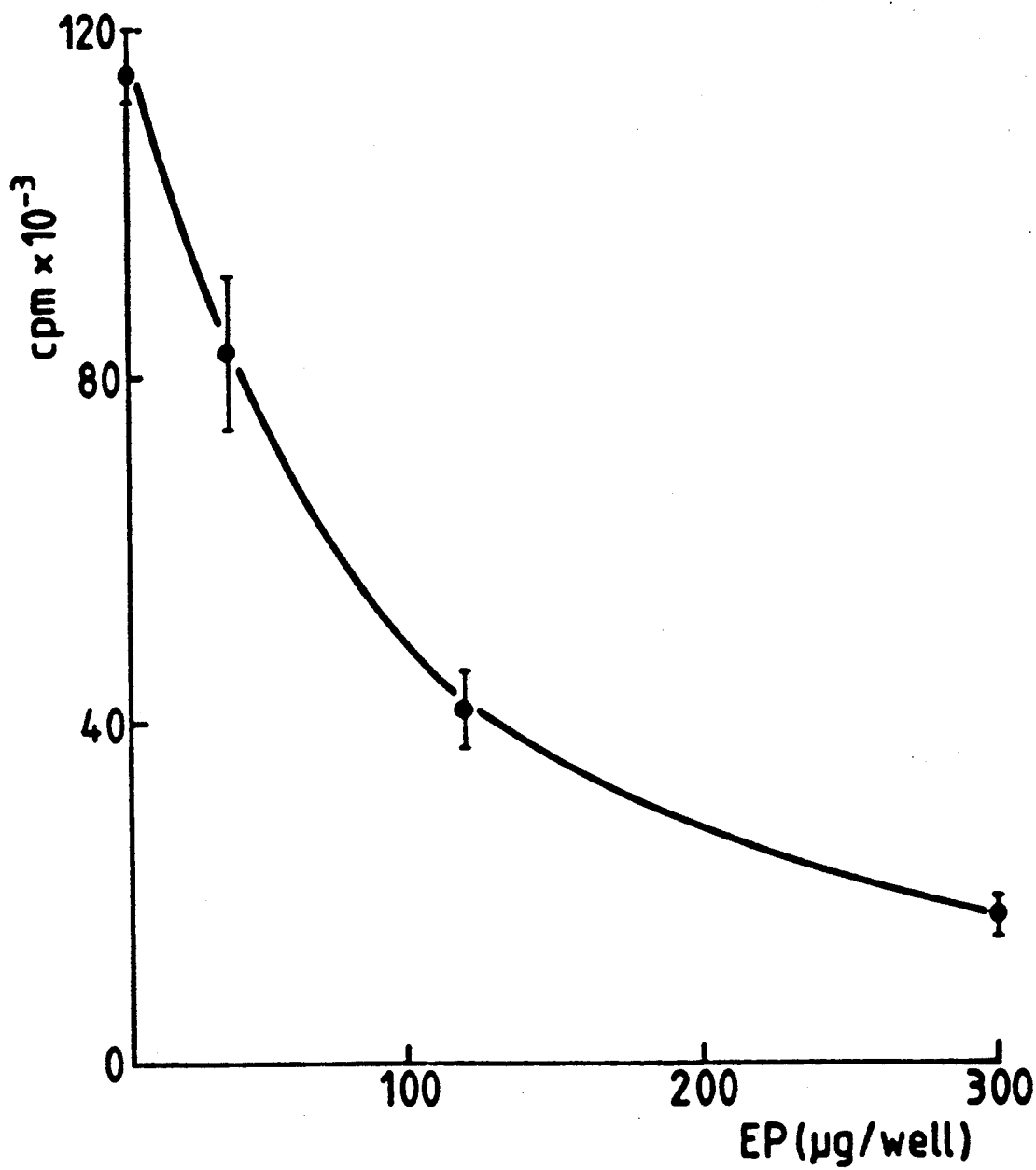
FIG. 2 is a graphical representation which shows the effect of various concentrations of the extrinsic glycoprotein preparation (EP) on mixed lymphocyte reaction (MLR).

FIG. 8, in four parts FIG. 8(a)1, FIG. 8(a)2, FIG. 8(b)1, and FIG. 8(b)2, is a graphical representation which shows the effect of the EP glycan glycoprotein extract and an EP oligosaccharide library (EPC) in FIGS. 8(a)1 and 8(a)2 on NK activity (NK Assay) and in FIGS. 8(b)1 and 8(b)2 on NC activity (NC Assay).

Figure 9:
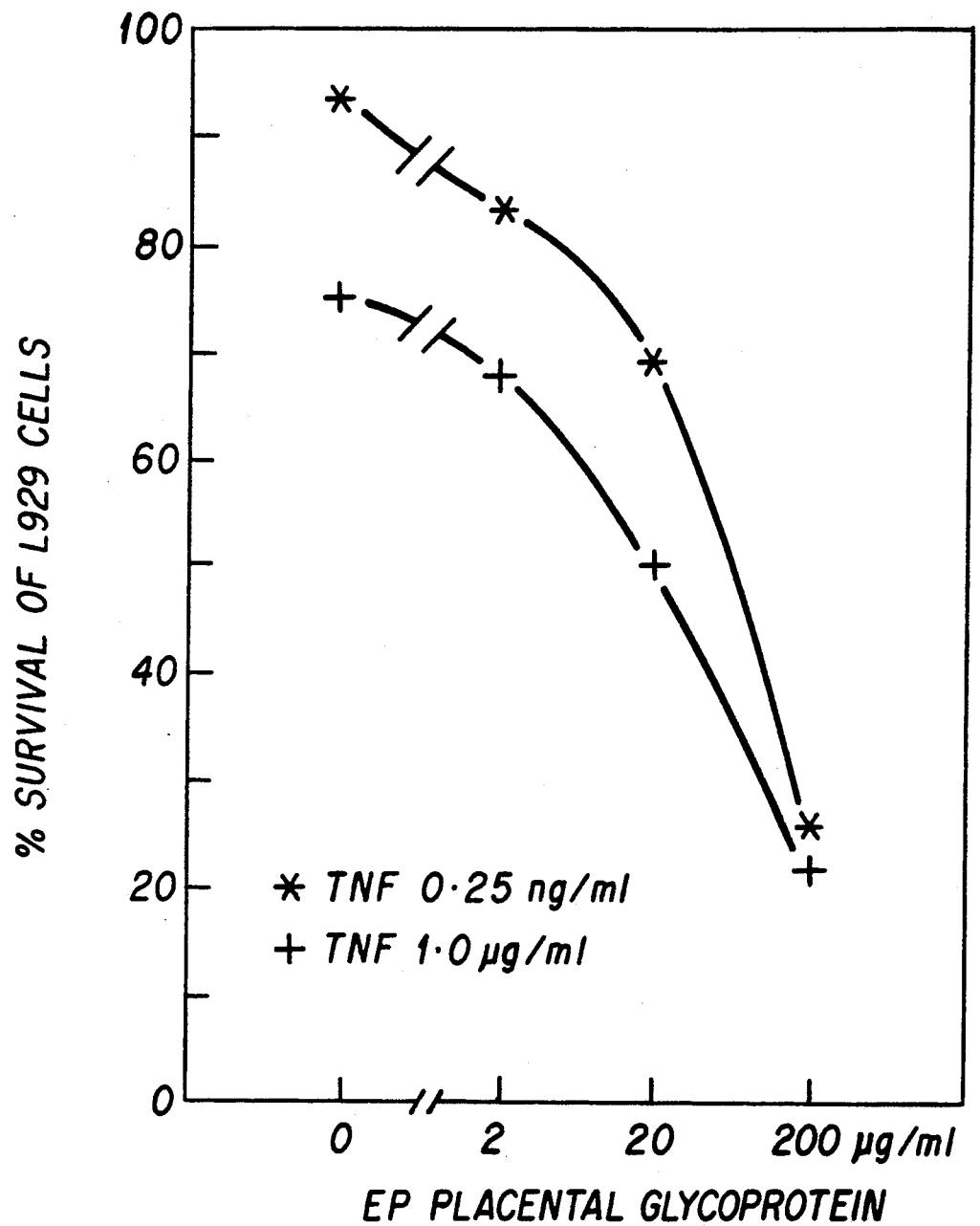

FIG. 9 is a graphical representation which shows the dose-related enhancement by placental glycoprotein (EP) of the toxicity for L929 cells at low concentrations of tumor neurosis factor (TNF).

Figure 10:
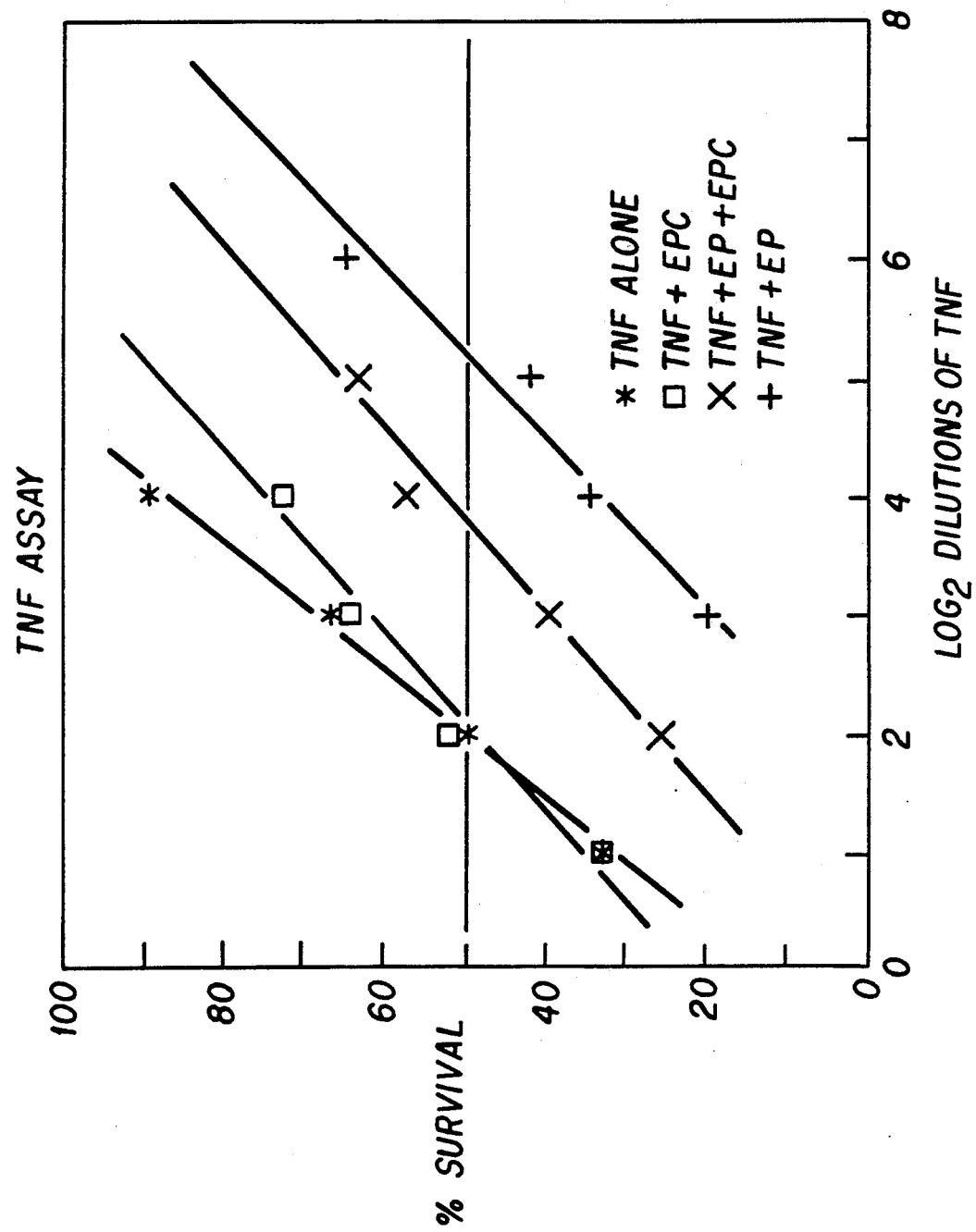

FIG. 10 is a graphical representation which shows the TNF dose-response curves obtained by emetine-treated L929 cells in the presence of medium alone (*); EP 50 μg/ml (+); EPC 16.7 μg/ml (□); or both EP and EPC (X).

Figure 11:
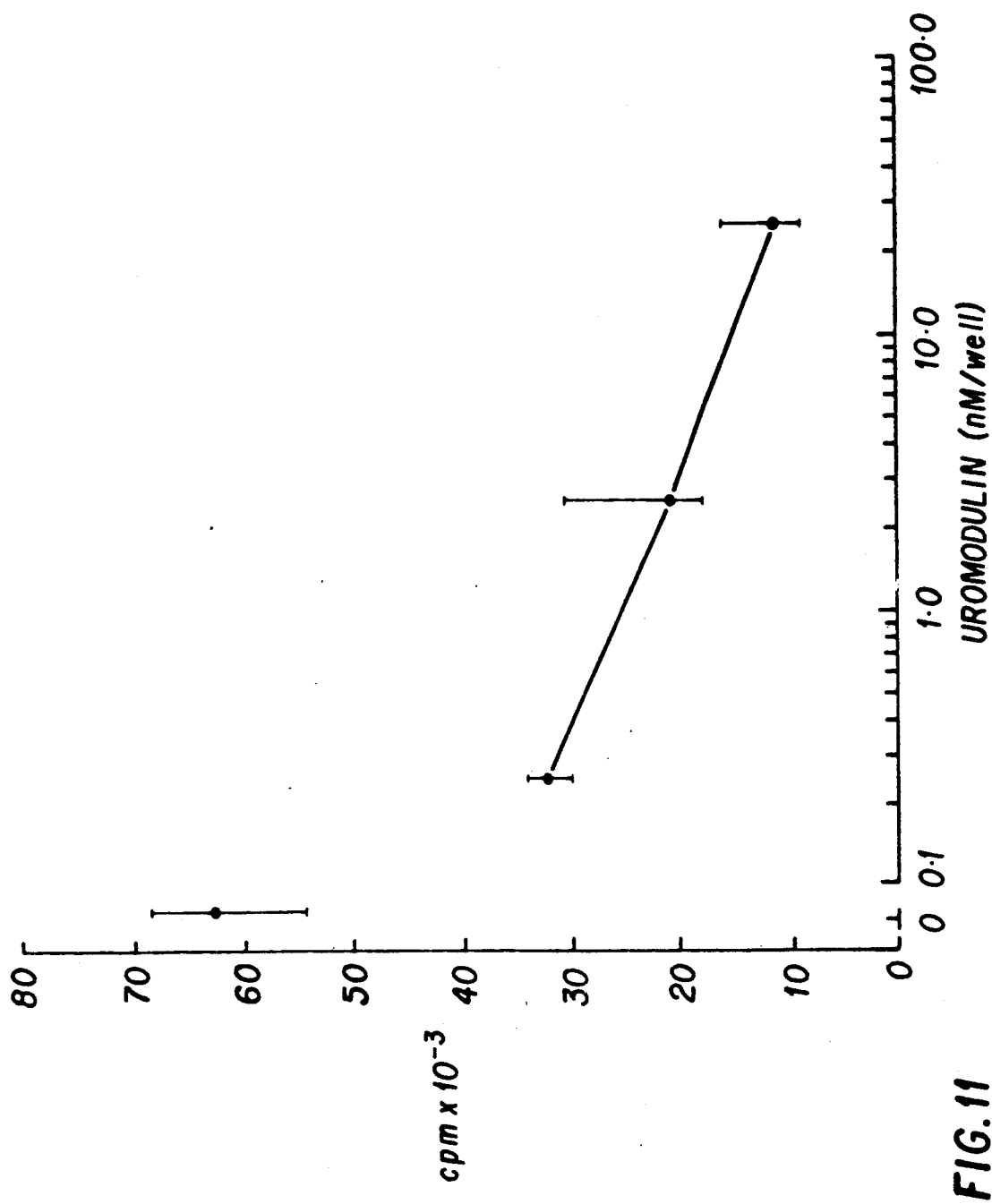

FIG. 11 is a graphical representation which shows the effect of uromodulin on MLR.

Figure 12C:
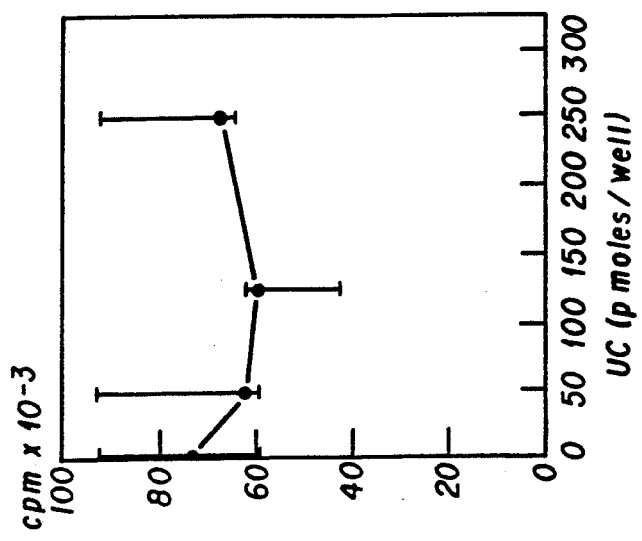
Figure 12B:
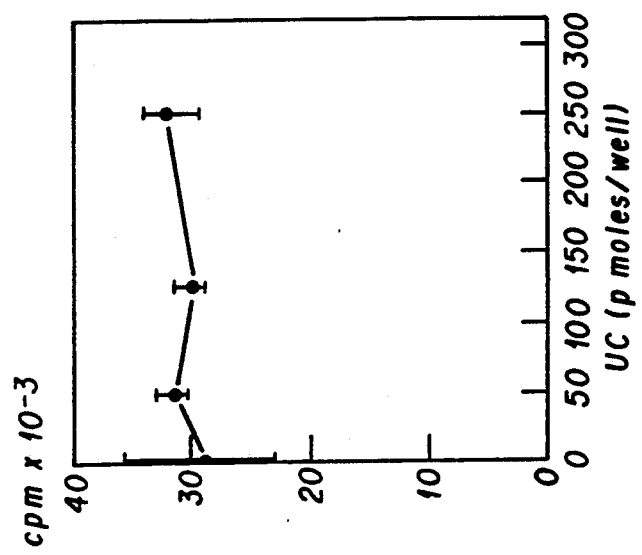
Figure 12A:
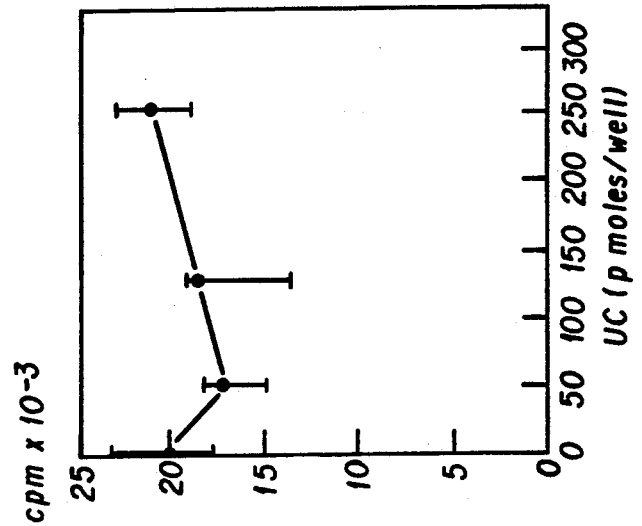

FIG. 12, in three parts, FIG. 12(a), FIG. 12(b) and FIG. 12(c), is a graphical representation which shows the effect of purified uromodulin oligosacchardies (UC) on three different MLRs in FIGS. 12(a), 12(b) and 12(c), respectively.

Figure 13A:
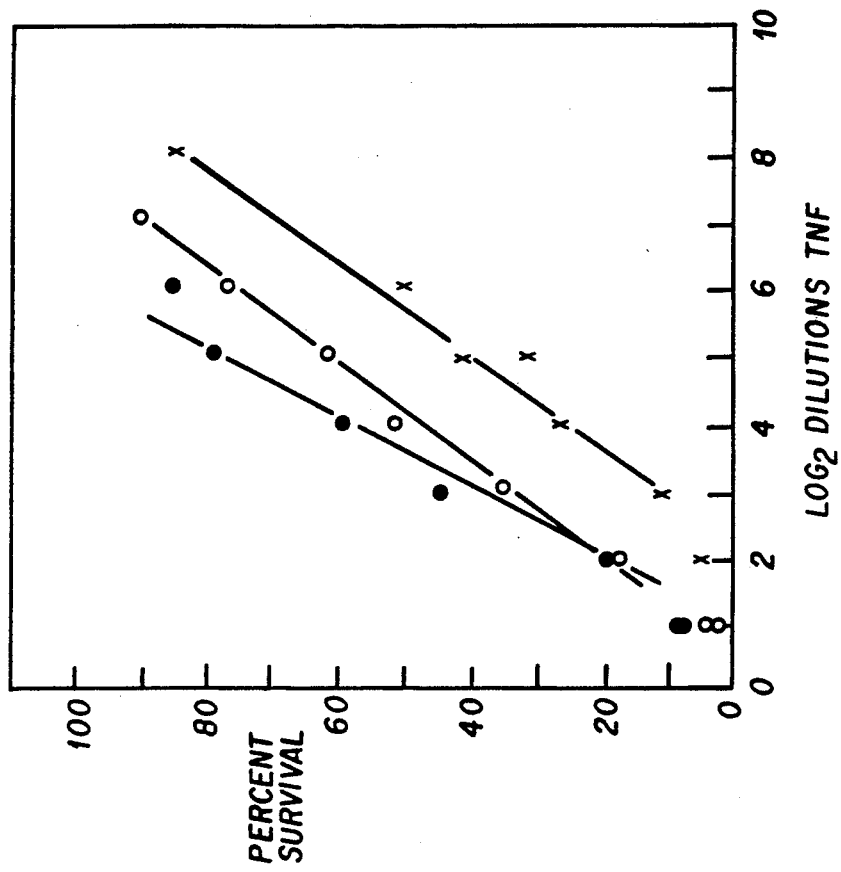
Figure 13B:
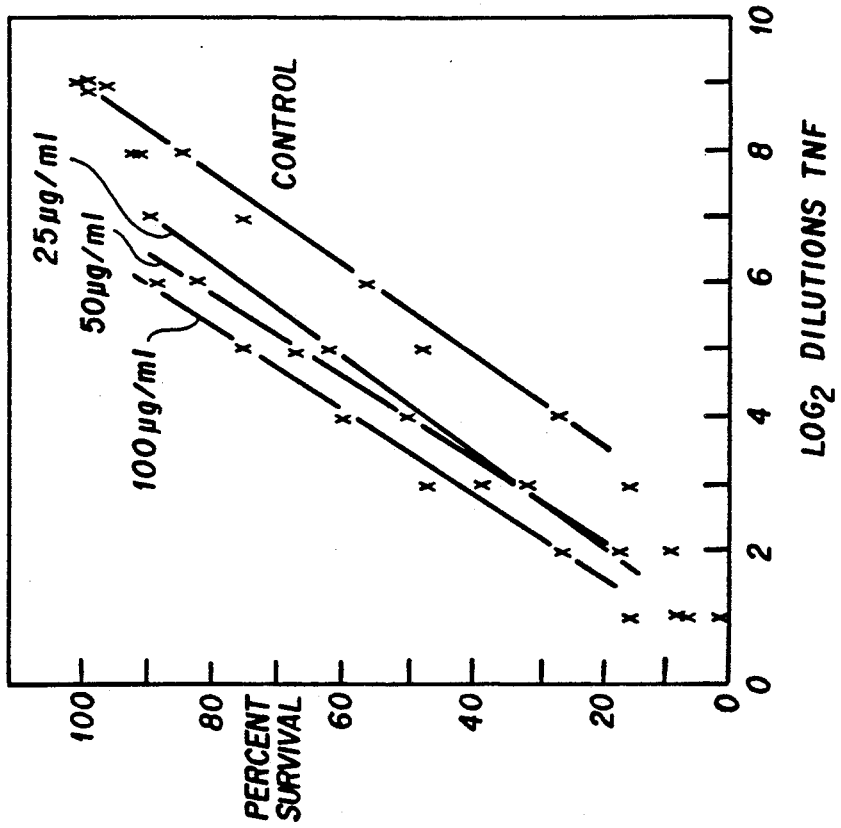

FIG. 13, in two parts, FIG. 13(a) and FIG. 13(b), is a graphical representation which shows the effect of Tamm-Horsfall (THf) glycoprotein on the activity of tumor necrosis factor in FIG. 13(a), 0 and 100 μg/ml THf in which the control, X, contains added THf, and in FIG. 13(b), 25, 50 and 100 μg/ml THf in which the control contains no added THf.

Initially, a relatively pure preparation of the syncytiotrophoblast microvilli membrane is made whereby the membrane is minutely subdivided and solubilized. Such pure preparations can be made as described by, for example, by Smith et al., Nature 252, 302-303 (1974). Particle size reduction can be carried out by conventional methods such as grinding, pulverizing or homogenization. Solubilization can be achieved by suspension of the resulting preparation in biologically acceptable aqueous solutions such as phosphate buffered saline (PBS) which preferably contains 3M KCl. A typical PBS comprises NaCl (120 mmol), KCl (2.7 mmol) and phosphate buffer salts (10 mmol), pH 7.4.

The unreduced N-linked oligosaccharides can be obtained from the solubilized membrane preparation by chemical release using anhydrous hydrazine. Preferred such isolation methods on a preparative scale are described in U.S. Pat. Nos. 4,719,294 and 4,236,022, the disclosures of which are incorporated herein by reference. These methods employ hydrazinolysis of the glycoprotein under reaction conditions to cause cleavage at the N-linked sites, producing a mixture having as a major component a de-N-acetylated hydrazone derivative of the oligosaccharides, followed by N-acylation of the hydrazone derivative, acid-catalysis of the hydrazone derivative, preferably followed by treatment with a stoichiometric amount of Cu(II) ions, to produce unreduced oligosaccharides, and subjecting the resulting unreduced oligosaccharides to cellulose chromatography to remove contaminants and recover the unreduced oligosaccharides.

Oligosaccharides thus released can be determined by the use of enzymes which are specific for their hydrolysis coupled with or followed by enzymic reactions which allow measurement of a product of hydrolysis. Thus, two useful enzymes for exoglycosidase digestion are Jack bean β-Nacetylhexosaminidase and Jack bean α-mannosidase which are commercially available from the Sigma Chemical Company (Poole, England) and can be further purified by adaptation of the method of Li and Li, Meth. Enzym. 28, 706 (1972). Jack bean β-Nacetylhexosaminidase cleaves all non-reducing terminal β-linked N-acetylglucosamine (GlcNAc) residues. Jack bean α-mannosidase will liberate one mannose (Man) from R-Manα-1→6(Manα→3)R' but none from R-Manα1→3(Manα1→6)R' R=H] as described by Yamashita et al., J. Biol. Chem. 255, 5635 (1980). Another useful enzyme is Jack bean β-galactosidase which can be purified from Jack bean meal and cleaves all non-reducing terminal galactose residues linked via a β1→4 glycosidic bond. Still another enzyme for the exoglycosidase digestion is the β-N-acetylhexosaminidase from Streptococcus pneumonia which can be purified by adaptation of the procedure of Glasgow et al, J. Biol. Chem. 252, 8615 (1977). This enzyme will cleave a non-reducing terminal GlcNAc residue if this is part of the structure.

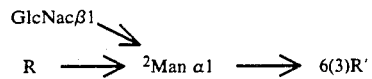

where R can be either H or FlcNAcβ1→4 as described by Yamashita, Biochem. Biophys. Res. Commun. 100, 226 (1981). So also, the enzyme α1→2 Mannosidase from Asperigillus phoenicis can be purified by adaptation of the procedure of Ichishima et al, Biochem. Biophys. Acta 658, 45 (1981). This enzyme will release non-reducing terminal mannose residues only if these are linked to the parent oligosaccharide via an α1→2 glycosidic bond as described by Yamashita et al., Biochem. Biophys. Res. Commun. 98, 1335 (1980). The following other exoglycosidases also can be obtained from commercial sources in a form sufficiently pure for sequence analysis: α-fucosidase from bovine epidydimis (Sigma Chemical Company, Poole, England), β-mannosidase from snail (Seikagaku Kogyo Company, Tokyo, Japan), and neuraminidase frfom Arthrobacter urefaciends (Calbiochem).

Asparagine-linked oligosaccharides which are released by the hydrazinolysis method, purified, tritium-labeled, treated with neuraminidase, and the resulting asialo oligosaccharides fractionated by the gel-permeation chromatography can then be analyzed by a sequence of exoglycosidase digestions with the foregoing enzymes. By comparing the initial elution positions and the exoglycosidase reactivity of oligosaccharides of known sequence, the structure of the released oligosaccharides can be determined. See, for example, Kobata in "Biology of Carbohydrates," Ginsberg and Robbins, Eds., John Wiley and Sons, pp. 87-162, 1984; Snider, Ibid., pp. 163-193.

In order to illustrate the isolation of the novel immunosuppressive agents in several embodiments of the invention in greater detail, an N-linked oligosaccharide library derived from syncytiotrophoblast microvilli membrane glycoproteins was prepared and tested as described in the following Examples. It will be appreciated that the invention is not limited to these specific embodiments or the details disclosed therein.

EXAMPLE 1

Syncytiotrophoblast microvilli membranes were isolated from human term placentae within one hour of delivery using the method of Smith et al., Nature 252, 302-303 (1974). Maternal placental cotelydons were dissected off, washed with 2 liters of 50 mM $CaCl_2$ and then 500 ml of phosphate buffered saline, minced, and added to 350 ml of 0.9% NaCl, pH 7.2, with stirring for 60 minutes at 4° C. A filtrate was then collected. Large cellular debris was removed by centrifugation at 800 g for 10 minutes and then 10,000 g for 10 min. Microvilli membranes were pelleted by centrifugation at 100,000 g for 45 min. Pellets from 30 normal term placentae were pooled and resuspended (20 ml/g membrane pellet) in phosphate buffered saline containing 3M KCl and stirred for 24 hours. The suspension was again centrifuged at 100,000 g for 45 minutes, the supernatant (EP) was recovered and extensively dialyzed against 85 mM Tris-HCl buffer, pH 7.4, containing 1 mM EDTA and 1% β-octylglucoside. The EP was chromatographed on a Zorbax GF250 HPLC column (4 micron, 150 angstrom, 25 cm×9.4 mm) running in the same buffer.

Table 1, below, shows that the microvilli preparations were found to have immunosuppressive activity which is also present in the retroplacental serum. No activity was found in the maternal serum. Most of the activity of the membrane preparations could be recovered in a 3M KCl extract (EP) of the membranes as shown in Table 1. FIG. 1 shows the HPLC chromatogram of EP in the presence of β-octylglucoside. In phosphate buffer the glycoproteins were found to aggregate and to elute in the void volume ($V_o$).

TABLE 1

| Preparation | Immunosuppressive activity* |
| --- | --- |
| Normal Human Serum | ** |
| Retroplacental serum | 36% |
| Maternal serum | 72% |
| Microvilli membrane | 600 μg/ml |
| EP | 350 μg/ml |

*Concentration required to give a 50% reduction of $^3$H-thymidine uptake in an MLR assay. See Example 3, below, for method.
**No activity present even at 100% serum.

EXAMPLE 2

This example describes a representative test of the effect of various concentration of EP on MLR in which the results are shown in FIG. 2. Syncytiotrophoblast microvilli membrane were isolated from human term placentae within one hour of delivery using the method of Smith et al., supra. Maternal placental cotelydons were dissected off, washed with 2 L 50 mM $CaCl_2$ and the 500 ml of phosphate buffered saline, minced, and added to 350 ml of 0.9 NaCl, pH 7.2, with stirring for 60 minutes at 4° C. A filtrate was then collected. Large cellular debri removed by centrifugation 800×g for 10 minutes and then 10,000×g for 10 min. Microvilli membranes were pelleted by centrifugation at 100,000×g for 45 min. Pellets from 30 normal term placentae were pooled and resuspended (20 ml/g membrane pellet) in phosphate buffered saline containing 3M KCl and stirred for 24 hours. The suspension was again centrifuged at 100,000×g for 45 minutes, the supernatant (EP) was recovered and extensively dialyzed against phosphate buffered saline. Mixed lymphocyte reactions (MLR) were performed as follows:

Blood was taken from two healthy male volunteers with differing class II MHC antigens into heparin prepared 50 ml plastic Falcon containers, diluted 1 in 3 with phosphate buffered saline and underlayered with Ficoll-Paquce ® (Pharmacia). After centrifugation at 500×g for 30 minutes, the buffy coat layer was recovered and washed twice with phosphate buffered saline. $1 \times 10^5$ cells from each donor was incubated in 200 μl of a solution containing RPMI 1640 cell culture medium with 1 mM glutamine, 10% heat inactivated foetal calf serum with or without the EP protein. Replicates (n=5) at each concentration were done in 96 well Cell-Cult microtitre plates (Sterilin, England). Cells were grown at 37° C. and 5% $CO_2$ for 6 days and 24 hour $^3$H-thymidine (Amersham) uptake was measured on the sixth day.

EXAMPLE 3

Figure 3:
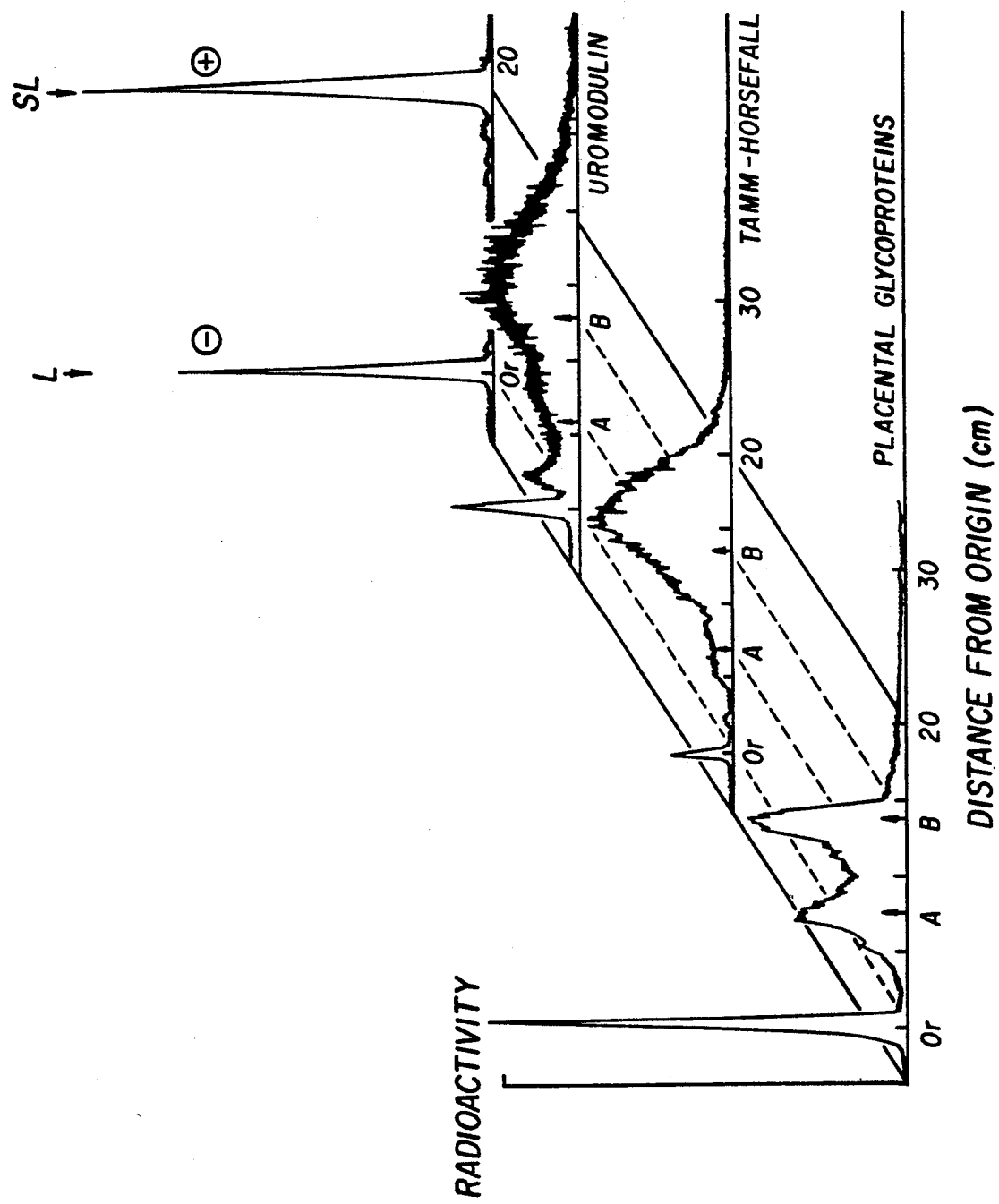
FIG. 3 is a graphical representation which shows the high-voltage paper electrophoretogram of the radioactive-labelled glycan libraries prepared from EP, Tamm-Horsfall protein and uromodulin.

This example presents the high-voltage paper electrophoretogram of the radioactive-labelled glycan libraries prepared from EP, Tamm-Horsfall protein and uromodulin as shown in FIG. 3. Tritium-labelled oligosaccharides were subjected to high-voltage paper electrophoresis (80 V $cm^1$) in pyridine/acetic acid/water (3:1:387 v/v/v), pH 5.4. The arrows indicate the positions to which [$^3$H] lactitol (L) and 6', 3'sialy[$^3$H]lactitol (SL) migrated. Tamm-Horsfall glycoprotein and uromodulin are the same protein isolated by two different methods as described by Hession et al., Science 237, 1479-1483 (1987) and Pennica et al., Science 236, 83 (1987).

EXAMPLE 4

Figure 4:
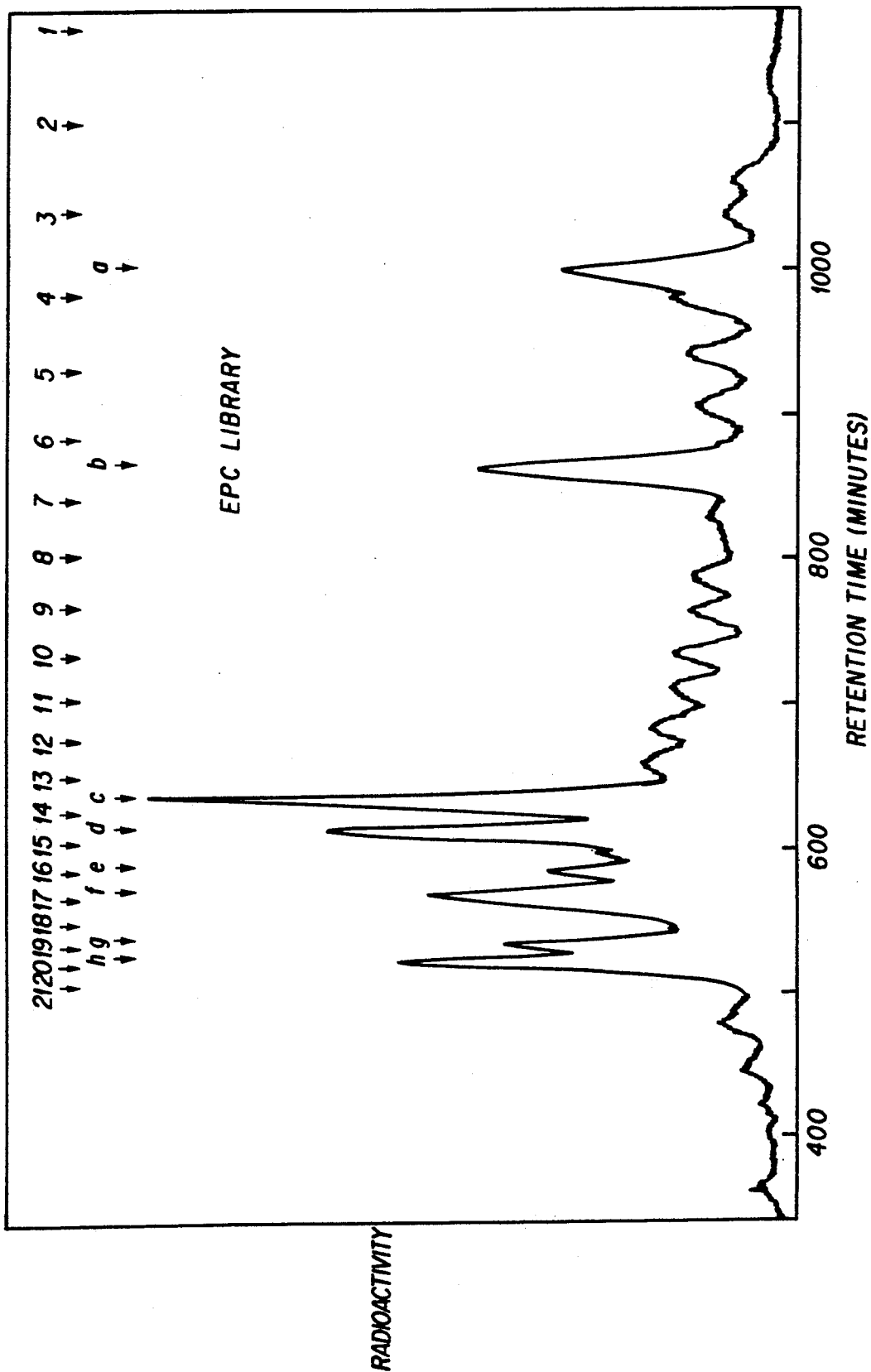
FIG. 4 is a graphical representation which shows the Bio-Gel P-4 (−400 mesh) gtel permeation chromatogram of the syncytiotrophoblast glycan (EPC) library following exhaustive sialidase digestion.

This example provides the preparative data for the Bio-Gel ® P-4 (−400 mesh) gel permeation chromatogram of the syncytiotrophoblast glycan library following exhaustive sialidase digestion as shown in FIG. 4. To prepare a total glycan library of the microvilli membrane the lyophilized salt-free unfractionated extrinsic glycoprotein preparation (EP) was cryogenically dried over activated charcoal at −196° C. ($<10^{-4}$ bar). The EP was dissolved in freshly doubled distilled anhydrous hydrazine (toluene/CaO 25° C., 10 Torr) under an anhydrous argon atmosphere. The temperature was 30° to 85° C. and then maintained at 85° C. for a further 12 h with shaking. The hydrazine was removed by evaporation under reduced pressure ($<10^5$ bar) at 25° C., followed by repeated (5×) flash evaporation from anhydrous toluene (thiophen and carbonyl free). The hydrozinolysates were N-acetylated by the addition of excess (5×amino groups) acetic anhydride (0.5M) in saturated $NaHCO_3$ at 4° C. for 10 min. The temperature was then raised to 25° C. and a second aliquot of acetic anhydride was added. The reaction was allowed to proceed for a further 50 min. Following N-acetylation, the samples were applied to a column of Dowex ® AG50 X12(H+) resin, eluted with water, and evaporated to dryness (27° C.). The desalted samples were dissolved in water and applied to Whatman 3 MM chromatography paper. Descending paper chromatography (27° C., 70% RH) was subsequently performed using n-butanol/ethanol/water (4:1:1 v/v) (solvent 1). After 48 h the first 5 cm measured from the origin were eluted with water. The oligosaccharides so isolated were flash-evaporated to dryness (27° C.), redissolved in cupric acetate (1 mM), incubated at room temperature for 1 hour, and subsequently eluted with water from a tandem column of Chelex 100 (Na+)/AG50 X12 (H+) resin and subjected to descending paper chromatography using solvent 1 for 1 day. The oligosaccharides were eluted from paper as described above, evaporated to dryness, redissolved in 4M acetic acid and chromatographed on an AG3.4A (OH—) resin column. An aliquot of eluted purified oligosaccharides were reduced with a 5-fold molar excess of 6 mM $NaBH_4$ in 50 mM NaOH adjusted to pH 11 with saturated boric acid (30° C., 4 h). An equivalent volume of 1M $NaBD_4$ in NaOH/boric acid, pH 11, was then added and the incubation continued for a further 2 h. The mixture was then acidified (pH 4–5) with 1M acetic acid and applied to a Dowex AG50 X12 (H+) column, eluted with water, evaporated to dryness (27° C.) and flash-evaporated (27° C.) from methanol (5×). The samples were then applied to Whatman 3 MM paper and subjected to descending paper chromatography for 2 days using solvent 1. Sialidase digestions were performed for 30 hours at 37° C. and desalted using a tandem column of Chelex 100 (Na+)/AG50 X12 (H+)/ AG3 4A (OH—)/QAE-sephadex and filtered through a 0.5μ teflon filter before being applied to Bio-Gel P-4 gel filtration columns.

The numerical superscripts refer to the elution position of glucose oligomers in glucose units as detected simultaneously by the refractive index monitor. Sample elution positions (in glucose units) were calculated by cubic spline interpolation between the internal standard glucose oligomer positions.

EXAMPLE 5

In accordance with this example, the unreduced glycan library was fractionated into acidic oligosaccharides (a). naturally occurring (b) or using Bio-Gel P-4 chromatography in water at 55° C. All acidic oligosaccharides were found to elute at $V_o$ when water was used as the running buffer. The acidic fraction ($V_o$) was then exhaustively digested with sialidase as described in Example 4 and fractionated on Bio-Gel P-4 chromatography.

EXAMPLE 6

This example describes a representative test of the effect of various concentrations of the syncytiotrophoblast glycan library on MLRs in which the results are shown in FIGS. 6(a)–6(f). MLRs were set up as described in Example 2. Proliferation was measured as a 24 hour tritiated thymidine uptake on day six of culture. Results are expressed as the medians and ranges of five replicates. Panels a–f show six different MLR's.

EXAMPLE 7

This example demonstrates the effect of the syncytiotrophoblast glycan library alone (solid line) and in conjunction with 100 μg of EP (dotted line) on a MLR. The MLR was set up as described in Example 2. Proliferation was measured as 24 hour tritiated thymidine uptake on day six of culture. The results are shown in FIGS. 7(a)–7(b) and expressed as the medians and ranges of five replicates. The different MLR's A and B are shown. The effect of EP alone is shown on the abscissus (top point).

EXAMPLE 8

This example demonstrates the effect of EP and EPC preparations in Natural Killer cell (NK) and Natural Cytotoxic cell (NC) assays as shown in FIGS. 8(a)1, 8(a)2, 8(b)1 and 8(b)2.

(a) Effect of the EP glycoprotein extract and EP the oligosaccharide library, EPC on NK (K562 target) activity using PBMNs as effector cells. The effector: target ratio was 50:1. Killing was measured as $^{51}Cr$ release. Results are expressed as median and range of 5 replicates.

(b) Effect of EP glycoprotein extract and an EP oligosaccharide library (EPC) on NC (WEHI-164 target) activity using PBMN's as effector cells. The effector: target ratio was 6.25:1. Killing was measured as described for NK assays.

EXAMPLE 9

This example illustrates the dose-related enhancement by placental glycoprotein (EP) of the toxicity for L929 cells at low concentrations of TNF (0.25 ng/ml; 1 ng/ml) as shown in FIG. 9. Data points are means of replicates which differed by less than 10%. The glycoprotein (EP) had no effect on L929 cells in the absence of TNF. The points plotted are means of replicates which differed by less than 10% so error bars are not shown. The test was repeated 10 times with similar results.

EXAMPLE 10

This example provides the preparative data for the TNF dose-response curves shown in FIG. 10. TNF dose-response curves were performed on emetine-treated L929 cells in the presence of medium alone (*); EP 50 μg/ml (+); EPC 16.7 μg/ml (□); or both EP and EPC (X). Briefly, L929 cells (a murine fibroblast line provided by Dr. N. Matthews, Cardiff University) in RPMI-1640 containing 5% FCS (Flow Laboratories, Irvine, Ayrshire) were seeded at $3 \times 10^4$ cells/well in 96 well microtitre plates (Nunc) and incubated overnight at 37° C. in an atmosphere of 5% $CO_2$ in air. Appropriate serial two-fold dilutons of a previously assayed batch of rTNF (from G. D. Searle Ltd.) of dilutions was chosen to span that which gave 50% kill of the L929 cells (defined as one unit of TNF activity). The medium in the wells was then replaced with 0.1 ml aliquots of these dilutions in duplicate. The glycoprotein (EP), free sugars (EPC) or control medium were added in further volumes of 0.1 ml, to identical TNF dilution series, giving a final volume of 0.3 ml/well. Cell survival was assessed 20 hours later as described previously. Percentage survival was then calculated with reference to control cultures incubated in medium alone, and a computer program used to perform regression analysis on the linear part of each TNF dose-responsive curve.

EXAMPLE 11

This example gives a representative plot of the effect of uromodulin isolated from urine of pregnant women on an MLR. Proliferation was measured as 24 hour tritiated thymidine uptake on day 6 of cultures. Results are shown in FIG. 11 and are expressed as the medians and ranges of 5 replicates. Uromodulin was isolated according to the method of Muchmore and Decker, *Science* 229, 479–481 (1988).

EXAMPLE 12

This example demonstrates the effect of purified uromodulin oligosaccharides (UC) on MLR's. The results for three different MLR's are shown in FIGS. 12(a)–12(c). Proliferation was measured as 24 hour tritiate thymidine uptake on day 6 of cultures. Results are expressed as the median and ranges of 5 replicates.

EXAMPLE 13

This example illustrates the effect of Tamm-Horsfall (THf) glycoprotein on the activity of TNF as shown in FIGS. 13(a)-13(b).

(Top). The symbols refer to the following X, control, O, 100 ug/ml THf isolated from the urine of a male.

(Bottom). Effect of increasing concentration of THf glycoprotein on the activity of TNF. The control contains no added THf. THf isolated from urine of normal male. The Tamm-Horsfall protein was isolated according to the method of Tamm and Horsfall, *J. Exp. Med.* 95, 71-97 (1952).

EXPLANATION OF RESULTS IN EXAMPLES 1-13

Pure preparations of placenta syncytiotrophoblast membrane microvilli were made by the method Smith et al., Nature 252, 302-303 (1974). Table 1 shows that this microvilli preparation had immunosuppressive activity which was also present in retroplacental serum. In contrast, only minimal activity was found in the maternal peripheral vein serum. Most of the activity of the membrane microvilli preparations could be recovered in a 3M KCl extract (EP) of the membranes as shown in Table 1. An HPLC chromatogram of the EP preparation in the presence of β-octylglucoside is shown in FIG. 1. In phosphate buffer the glycoproteins were found to aggregate and to elute in the void volume. Western blotting with anti-THf (Tamm-Horsfall) antibody following SDS-PAGE showed the presence of only a small quantity of antibody reactive material migrating at 85-kDa. This demonstrated that EP was not identical to the Tamm-Horsfall (uromodulin) glycoprotein, which has previously been proposed to be immunosuppressive by Muchmore and Decker, *J. Immunol.* 138, 2541-2545 (1987). A dose dependent reduction in the proliferation of peripheral blood mononuclear cells stimulated by MLR was found with increasing concentrations of EP and is shown in FIG. 2. This effect could be blocked by the addition of increasing amounts of IL-2 to the cultures.

To determine if the attached glycans were functionally important in suppression of MLR by EP an oligosaccharide library was prepared from the EP preparation by chemical release using anhydrous hydrazine as described by Ashford et al., *Eur. J. Biochem.* 166, 311-320 (1987). The high-voltage radio-electrophoretogram and Bio-Gel P-4 profile for the oligosaccharides present in EP are shown in FIGS. 3 and 4 respectively. The HVE electrophoretogram demonstrates that the EP contains both neutral and acid oligosaccharides. FIG. 3 also shows the HVE profile of the oligosaccharides present on Tamm-Horsfall and uromodulin which differ from the EP preparation. Neuraminidase digestion of the acidic EP sugars (72%) completely converted the acidic structures to neutral components indicating that the charged groups present in EP were exclusively sialic acid and not phosphate or sulfate.

The Bio-Gel P-4 chromatogram shown in FIG. 4 shows the elution positions and relative molar proportions of the $NaB^3H_4$ reduced oligosaccharides relative to a dextran hydrolysate. The EP oligosaccharide library was incubated with neuraminidase prior to the chromatographic separation. FIGS. 5(a)-5(b) shows the Bio-Gel P-4 chromatogram of the naturally occurring neutral and acidic moieties. This figure illustrates that both O-linked and N-linked glycans are present in the library. The only structures (post-sialidase) in common between the neutral and acidic oligosaccharides are fractions 1 and k which correspond to biantennary-complex oligosaccharides with and without core-fucose respectively. The shoulder on peak 1 in FIG. 5(b) suggests the presence of a 'bisecting' GlcNAc in some of the structures. The majority of the remaining structures in the neutral fraction are of the oligomannose or hybrid type. Of particular interest are the presence of unusual oligomannose structures, that is $Man_2GlcNAc_2$ (fraction c). $Man_3GlcNAc_2$ (fraction d) $Man_4GlcNAc_2$ (fraction e). Structural analysis of uromodulin and Tamm-Horsfall showed predominantly complex-type oligosaccharides. The only oligomannose structures isolated from Tamm-Horsfall was $Man_6GlcNAc_2$. In contrast, $Man_5GlcNAc_2$ and $Man_6GlcNAc_2$ were present on uromodulin. The profile of the complex-type oligosaccharides was essentially identical between Tamm-Horsfall and uromodulin.

The EP oligosaccharide library had no effect on MLRs when added alone (FIGS. 6(a)-6(f) sugar library was able to completely reverse the inhibitory effect of the EP glycoprotein extract FIGS. 7(a)-7(b). The amount of sugar added was determined by co-reduction with $NaB^3H_4$ of an aliquot of the unreduced preparation and N,N'-di-acetylchitobiose. Since not all structures will be active, the concentration of oligosaccharide required to block the activity of EP can only be estimated to be $\sim 10^9$ M. The effect of EP and EPC on Natural Killer cell (NK) and Natural Cytotoxic cell (NC) activities was also assessed to determine the specificity of the MLR suppression by EP. FIGS. 8(a)1, 8(a)2, 8(b)1, 8(b)2 show that neither EP or EPC had any effect, either inhibitory or stimulatory in these assays.

In order to discover whether the placental glycoprotein wa able to interact with cytokines its effect on TNF toxicity was measured. The EP preparation was added to doubling dilutions of recombinant TNF (rTNF) in a modification of the standard assay of Rook et al. The addition of EP to L929 cell cultures had no effect on survival at concentrations between 2 and 200 μg/ml. Higher concentrations were not tried. However EP enchanced the toxic effect of TNF in a dose-related manner (FIGS. 9 and 10). Thus doses of TNF which when used alone were minimally toxic for L929 cells (93.4% and 75.4% survival) became progressively more toxic as the concentration of EP was increased (FIG. 9) resulting in only 25.5% and 21.8% survival when 200 μg/ml of EP were present. FIG. 10 shows a similar test in which EP was added at a single concentration (50 μg/ml) to a series of doubling dilutions of TNF. The concentration of TNF giving 50% survival was defined as one unit/ml. In the presence of EP at 50 μg/ml one unit had the toxic activity of 9.2 units. In contrast the free sugars at 16.7 μg/ml had no effect. However, when both EP and EPC were added at these concentrations, inhibition of the EP-induced enhancement was seen, so that one TNF unit became equivalent to 3.5 units rather than 9.2 units.

The foregoing results suggest that the syncytiotrophoblast contains membrane associated glycoproteins which are able to specifically suppress immune-responses secondary to genetic maternal-foetal incompatibility without affecting other afferent arms of the immune repertoire, i.e. NC and NK cells. Such a mechanism is consistent with the concept of an immuneprivileged tissue. The lack of bioactivity of the oligosaccharides derived from these membrane glycoproteins probably reflects their monovalent state. Consistent with this is the finding that they were able to block the immunosuppressive activity of their parent glycoproteins. The reason that IL-2 is also able to block the immunosuppressive effect is at present unknown.

Muchmore and Decker, *Science* 229, 479-481 (1985), have previously reported that uromodulin (ConA preparation of Tamm-Horsfall) is an immunosuppressive protein. They reported that uromodulin was able to inhibit PHA mitogen induced proliferation and proposed that this effect was due to inhibition of IL-1 (binding constant of uromodulin to IL-1 of $10^{-11}$ M) [Brown et al., *Proc. Natl Acad. Sci. U.S.A.* 83, 9119-9123 (1986)]. Muchmore et al., *J. Immunol.* 138, 2541-2545 (1987), Ibid. 2547-2555 (1987), also reported that the oliogsaccharides from uromodulin were themselves immunosuppressive. Data has now been present which suggests that these results are artefactual. Moonen and Williamson, *J. Immunol. Methods* 102, 283-284 (1987), have suggested that since PHA is known to bind to Tamm-Horsfall glycoprotein, the inhibition of PHA-induced lymphocyte proliferation cannot be assumed to be due to inhibition of IL-1 even if IL-1 binds to uromodulin. Moonen et al., *FEBS Lett.* 226, 314-318 (1988), have recently presented data which shows that in fact native IL-1 or TNF do not bind to uromodulin. Their results suggest that uromodulin interacts with denatured cytokines but not native soluble cytokines. However, the ability of uromodulin to bind membrane bound IL-1 still needs to be determined. FIG. 11 shows that uromodulin is able to suppress the MLR, however, the free oligosaccharides had no bioactivity (FIGS. 12(a)-12(c)). Further, FIG. 13 shows that the presence of Tamm-Horsfall glycoprotein has no effect on TNF toxicity but was found to slightly inhibit (one $log_2$ dilution). This latter result is in contrast with the work of Sherblom et al., *J. Biol. Chem.* 263, 5419-5423 (1988), who showed that uromodulin had no effect on TNF cytotoxic activity. In either case, these tests demonstrate that the properties of EP differ from purified uromodulin (THf).

The effects of the EP glycoprotein on TNF activity suggest that the activity of cytokines (e.g. TNF) are determined not only by their concentrations, but also by their binding to a group of regulatory glycoproteins. Changes in level of these glycoproteins, or in their glycosylation may have profound relevance to a variety of toxic and cachetic syndromes. This concept is consistent with the wider clinical literature which suggests the presence of 'factors' which affect the clincial impact of cytokine release (e.g. tumor associated cachexia, liver disease, Shwartzman reaction etc.) See Rothstein et al., *Proc. Natl. Acad. Sci. U.S.A.* 85, 607-611 (1988); Lehman et al., *J. Exp. Med.* 164, 657-663 (1987); Onwubalili et al., *J. Med.* 230, 599-610 (1986); Beutler and Cerami, In: *Ann. Rev. Immunol.* 7, 625-55 (1989), ed. Paul.

The finding of a placenta associated glycoprotein which is both immunosuppressive and able to act synergistically with TNF is unexpected. It is claimed that the TNF gene is active in all foetal tissues, suggesting that its true biological role has something to do with tissue remodeling. TNF can be detected in amniotic fluid by immunoassay, but not by bioassay, suggesting that it is bound to an inactivator, or cleaved to inactive fragments [Jaattela et al., *Immunobiology* 175, 111-112 (1987)]. There is likely to be a mechanism for protecting the mother from foetus-derived TNF.

Various other examples will be apparent to the person skilled in the art after reading the present disclosure without departing from the spirit and scope of the invention, and it is intended that all such other examples be included within the scope of the appended claims.

What is claimed:

1. An immunosuppressive glycoprotein having a sugar composition comprising oligosaccharides which upon release from the protein moiety and following digestion with neuraminidase exhibit an elution profile upon polyacrylamide gel permeation chromatography as shown in FIGS. 4 or 5.

* * * * *

UNITED STATES PATENT AND TRADEMARK OFFICE
CERTIFICATE OF CORRECTION

PATENT NO. : 5,109,116

DATED : April 28, 1992

INVENTOR(S) : PETER D. ARKWRIGHT ET AL.

It is certified that error appears in the above-identified patent and that said Letters Patent is hereby corrected as shown below:

In col. 5, line 60, after "debri" insert --was--.  In col. 6, line 7 "Paquce" should read --Paque--.  In col. 6, line 46, after "The temperature was" insert --raised 17°C/h from--.  In col. 10, line 23, after "6(f)" insert --but the--; line 38, "wa" should read --was--.

Signed and Sealed this

Twenty-first Day of September, 1993

*Attest:*

BRUCE LEHMAN

*Attesting Officer*    *Commissioner of Patents and Trademarks*